United States Patent [19]

Capots et al.

[11] 4,322,678

[45] Mar. 30, 1982

[54] IDENTIFICATION OF MATERIALS USING THEIR COMPLEX DIELECTRIC RESPONSE

[76] Inventors: Larry H. Capots, 8622 Chapel Dr., Annandale, Va. 22003; James George, 809 W. Broad St., Falls Church, Va. 22046; Luigi Morelli, 305 E. Davis St., Sterling, Va. 22170

[21] Appl. No.: 89,296

[22] Filed: Oct. 30, 1979

[30] Foreign Application Priority Data

Oct. 30, 1978 [IT] Italy ............................... 29252 A/78

[51] Int. Cl.³ ........................................ G01R 27/26
[52] U.S. Cl. ............................. 324/61 R; 324/DIG. 1
[58] Field of Search ............ 324/61 R, 61 QS, 65 R, 324/57 SS, DIG. 1; 86/1 B; 340/200

[56] References Cited

U.S. PATENT DOCUMENTS

| | | | |
|---|---|---|---|
| 3,155,898 | 11/1964 | Chope | 324/61 R X |
| 3,255,410 | 6/1966 | Norwich | 324/61 R |
| 3,323,049 | 5/1967 | Hanken | 324/61 R |
| 3,684,952 | 8/1972 | Lundstrom | 324/61 QS |
| 3,876,916 | 4/1975 | Stoakes | 324/61 R X |
| 4,174,498 | 11/1979 | Preikschat | 324/61 R X |

*Primary Examiner*—Stanley T. Krawczewicz
*Attorney, Agent, or Firm*—John J. Byrne

[57] ABSTRACT

The non-linear conductance and capacitance characteristics of electrically non-homogeneous materials over a given frequency range are used to identify and analyze such materials.

10 Claims, 10 Drawing Figures

IDENTIFICATION OF MATERIALS USING THEIR COMPLEX DIELECTRIC RESPONSE

BACKGROUND OF INVENTION

This invention relates to testing of materials, particularly materials which are non-homogenous.

These materials are mixtures of two or more component materials, each of which has a very different electrical conductivity and dielectric constant. Materials so composed, because of their electrical properties, are often termed non-homogenous. Some examples of these kinds of materials are explosives, which are composed of the explosive molecule with high dielectric constant and an inert filler such as sawdust which has a comparatively low dielectric constant; another example is the mixture of water and soil, which may appear uniform in consistency, yet water and soil have clearly different electrical characteristics.

Further examples are water and suspended solids or even marbleized meat where the component elements in this case are lean muscle tissue and fatty tissue.

There has been a long-standing need for a rapid non-destructive test of non-homogenous materials that will readily identify them or give their properties. Two immediate applications for such tests are in the field of letter bomb detection and in soil analysis.

With respect to security detection, the ability to package explosives in small envelopes, and them them through the mail has presented a long-standing security problem. With respect to soil analysis, there is a need for a rapid soil test in the field, which will give information regarding moisture content or mechanical properties.

It has been found that both of these materials have distinct conductive characteristics which are non-linear over given frequency ranges. This information can be used to identify and analyze such materials.

SUMMARY AND FEATURES OF INVENTION

Accordingly, this invention is directed to providing a nondestructive test for non-homogenous materials, a constituent of which has a high dielectric property.

It further provides an electronic test apparatus wherein the electrical properties of the material are used to give information with regard to its type and composition.

A feature of this invention is the use of the conductive properties of non-homogenous materials to provide a means for testing.

A still further feature of this invention is the ability to test materials in a closed container.

Another feature of this invention is the provision of a testing capability which will identify explosives in packages such as letters.

A still further feature of this invention is to provide a testing technique which gives almost instantaneous readings and permits scanning of many objects at a very high rate.

Another feature of this device is the use of conductive curve data based on frequency response to distinguish non-homogenous types of material having high dielectric elements from other types of material.

Another feature of this invention is the use of conductive level response and slope of the conductive curve to distinguish various types of material, and to give information on concentration of the high dielectric element within the composition.

A still further feature of this invention is to provide apparatus which will permit determination of the moisture content in non-homogenous materials, such as soils.

THE DESCRIPTION OF THE INVENTION

Figure 1:
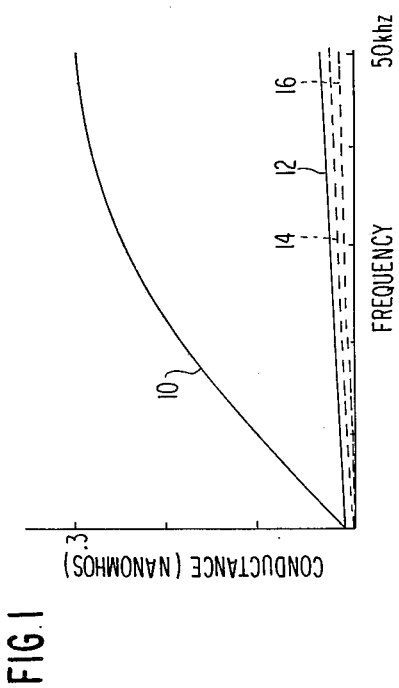
FIG. 1 shows conductance versus frequency curves and illustrates the conductance response of several explosives as compared to other materials.
Figure 2:
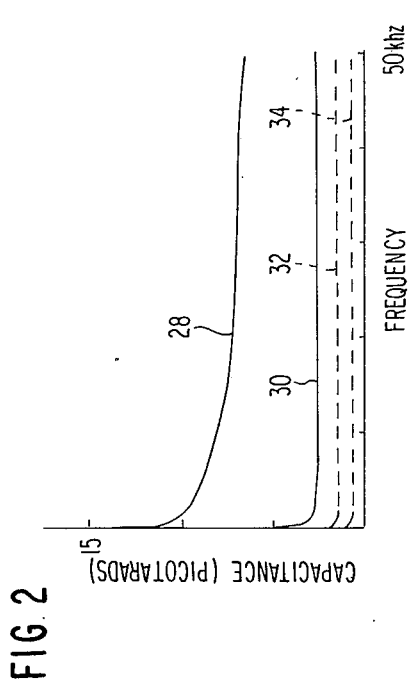
FIG. 2 is a plot of conductance versus frequency for several explosives and non-explosive material which illustrates the higher conductance level for explosives.

Referring particularly to the drawings, FIGS. 1 and 2 show conductance versus frequency curves for envelopes containing explosives and non-explosive materials. The curves were obtained by placing the envelope between two flat spaced plates which form a capacitive element and are part of a conductance sensitive electronic circuit.

In FIG. 1, the curve 10 is for the explosive compound PETN and shows a capacitive value for frequencies to fifty kilohertz. Note that the conductance rises sharply for PETN to a value of 0.3 nanohms at which point it levels out.

The solid line 14 is for an envelope containing the explosive Compound C which has a higher conductance level than the two dashed lines which are respectively the curves for envelopes containing plexiglass and paper.

FIG. 2 also shows conductance vs. frequency curves for explosive substances as a solid curve and non-explosive substances as dashed curves. It will be noted that the conductance values on this graph are tenfold greater than those of the curves in FIG. 1. This scale clearly shows the higher conductive level for the explosive Compound C shown in line 18, and for dynamite 19. Curve 20 is for plexiglass within an envelope and is lower than curves 18 and 19. Curve 22 has a lower conductance yet, and it obtained for an envelope which contains both paper and coins. Curve 24 is the curve for a plain envelope with paper, and curve 26 is obtained for an envelope which contains paper and two credit cards.

These figures show the large conductance change of explosive materials as a function of frequency, particularly with respect to PETN and dynamite. With respect to Compound C, it will also be noted that there is a large conductance change with frequency for this material in the lower frequency range as illustrated in FIG. 2.

On the contrary, non-explosive substances show a much lower change in conductance for change in frequency.

The explosive materials are a mixture of a blinder with an explosive. The explosive has very high dielectric properties and has a large non-linear loss component over a frequency range up to approximately fifteen kilohertz.

Figure 3:
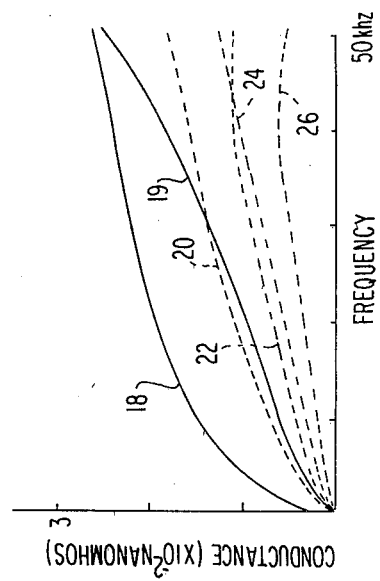
FIG. 3 is a capacitance versus frequency diagram showing curves for several explosives and non-explosives.

The capacitive values are proportional to the permitivity of the sample inserted between the plates. As seen in FIG. 3, the plots of capacitance versus frequency from approximately one hundred hertz to fifty kilohertz shows that the explosives shown in solid line have a permitivity which has some frequency dependence, and that the capacitance is much larger in value than that for non-explosive samples shown in dotted outline. The curve for the explosive PETN is shown at 28, and the curve for Compound C is shown at 30. Curves 32 and 34 respectively show the results obtained for envelopes containing plexiglass alone and for an envelope containing two credit cards.

Figure 4:
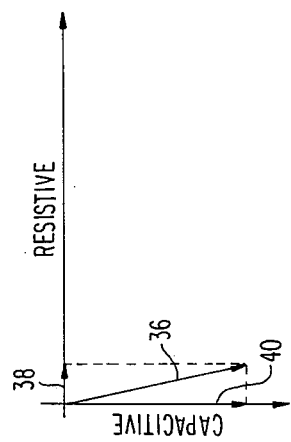
FIG. 4 is a vector diagram for a typical capacitive component which shows both the capacitive and resistive components, both of which are of interest.

The significance of this property of non-homogenous material having a high dielectric element is illustrated in FIG. 4. The electrical vector 36 representing the large loss across the plates of the capacitor has a capacitive component 40 and a resistive component 38. The capacitive component contains information with respect to the dielectric constant. The resistive component 38 provides basic information with respect to the resistive value of the loss. Different measurements are obtained for each frequency applied in a range from up to fifty kilohertz for a given sample which is placed between the plates of the capacitive element. With the resistive component a value can be found for the resistance at each frequency. The conductance is merely a reciprocal of this value.

Explosive materials have been found to have a nonlinear conductance curve. They are a mixture of the unstable explosive compound having a high dielectric constant, and an inert filler such as sawdust which does not have such a property.

The conductance curve for each type of explosive is distinctive.

Figure 5:
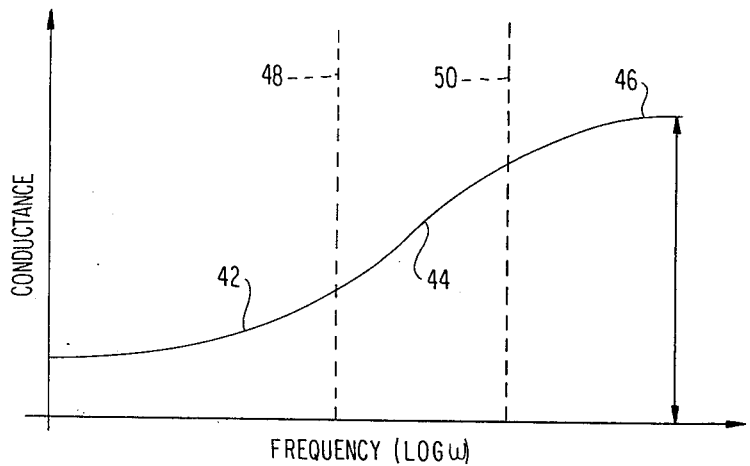
FIG. 5 is a graph of a typical curve for explosives showing the rate of change in the conductance curve with respect to concentration of explosives.

In FIG. 5, the variation in conductance as plotted against the log value of frequency produces a somewhat S-shaped curve. Factors which are of interest are the rate at which the cnductance increases with frequency, and the point at which the conductance reaches a maximum. The rate of change of these curves is a function of the volume concentration of the high dielectric material (explosive) in the filler. The magnitude of the curve where the rate of change becomes zero is related to the amount of high dielectric property material, as well as its volume concentration.

The lower section of the curve 42 shown in FIG. 5 has a gradual rise to the middle portion 44 and a leveling out of the curve at 46. Midportion of the curve 44 between the dashed lines 48 and 50 shows the change of rate of conductance with frequency. This portion of the curve is related to the concentration of the dielectric element in the composition.

The leveling out point of the curve at the upper portion of 46 is related to both the volume concentration and the amoount of material.

It has been found that each type of material has its own distinctive conductance curve, and therefore different types of material can be distinguished one from another after various sets of reference curves have been obtained. These distinctive conductance curves or signatures make it possible to scan a package such as an envelope without opening it, and to specifically identify both the amount and type of material within the envelope or package.

Figure 6:
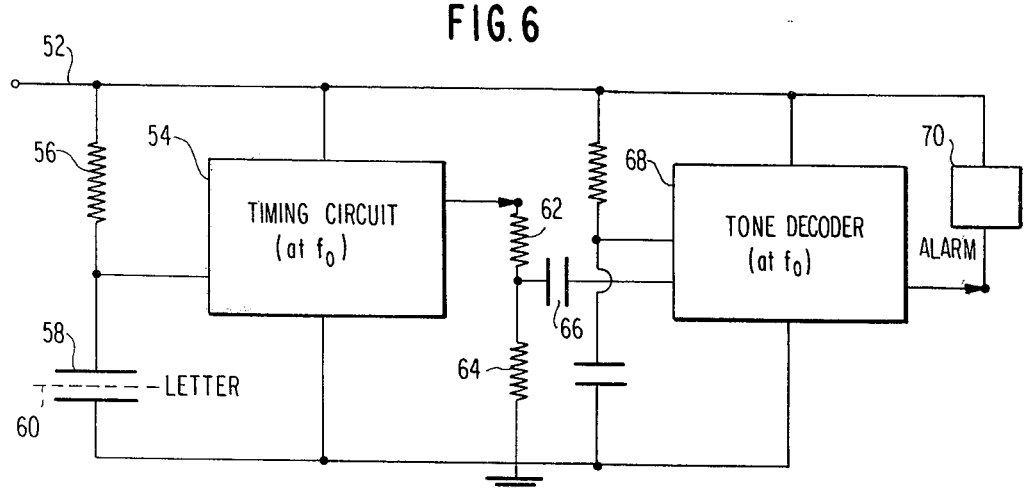
FIG. 6 illustrates a circuit for detecting change in conductance which uses a timing circuit and a tone decoder.

There are a number of different electrical circuits that can be used to take advantage of the conductive characteristics of the non-homogenous dielectric containing materials. One such circuit is shown in FIG. 6. This circuit is expressly directed toward examining letters for those that might contain explosives.

An input line 52 is connected in parallel to a timing circuit 54 and with a line containing a resistance 56 and a capacitive element 58. The capacitive element 58 consists of two parallel spaced plates between which a closed letter 60 is passed.

The R-C circuit formed by the resistance 56 and the capacitive element 58 affect the timing circuit 54 when there is a change in value of the capacitive element 58. The introduction of a letter 60 containing a high dielectric material does this. Inasmuch as the capacitive element does not represent a pure conductance, the equivalent circuit of this element is a capacitance in parallel with a resistor. The voltage component would be essentially as shown in FIG. 4, in which the dominant term for the vector is the capacitive component.

The explosive causes a large change in the conductive value and therefore changes the frequency output of the timing circuit 54. When the plates of capacitive element 58 do not have an object between them the timer frequency is a certain given value. This output is fed through the resistive network 62 and 64 and is coupled through capacitor 66 to the tone decoder. The tone decoder is turned to this frequency which is represented as $f_o$. When the two frequencies are in tune the tone decoder output is high.

However, when a material containing a high dielectric type substance (explosive) is inserted between the plates, the capacitance of the element 58 changes. This is because of the change in permitivity caused by the high dielectric material. Therefore, since the equivalent circuit represents a capacitance and resistance in parallel, vector measurements to determine both the capacitive and resistive components (FIG. 4) are of interest. The accurate measurement of the resistive component, which is the reciprocal of conductance will give a conductance value.

Since the charging time for the capacitive element 58 of the R-C network of the timing circuit changes, the output of the timing circuit changes also. The magnitude of this difference is large enough to exceed the band width of the tone decoder. The tone decoder output consequently is lowered, and the alarm circuit 70 which is made to sense such changes is activated.

The values can be selected so that the sensitivity of the circuit can be changed to suit the items being scanned. The given circuit can readily be varied if desired by varying the band width of the decoder 68.

The frequency applied to the circuit through line 52 will be between thirty to fifty kilohertz for explosives. This can be seen by referring to FIGS. 1 to 3, the higher conductive and capacitive reaction of explosives is readily distinguishable.

The circuit is also fast acting. For example, when it is used as a letter bomb detector on the order of from 700 to 1000 pieces can be scanned per minute.

If identification of the explosive were required, a signature curve would have to be generated by applying a plural number of frequencies. The simple letter bomb detector operates on a single frequency in which the conductance level or capacitance change (loss) is used to determine presence of any explosive since all conductance readings will be high.

Construction of the plates of the capacitive element 58 when used as a letter bomb detector can be almost envelope size. The plates used were thin metal three inches wide and eleven inches long and were parallel speed about half an inch apart.

The phase angle of the frequency applied to the circuit with reference to the frequency applied across the capacitive element 58 is also of importance. They should be within one-half a degree of being in phase or be corrected for such situation in order to get good accurate readings. It is further essential that a very stable fixed oscillator signal be used to get clear accurate readings.

Figure 7:
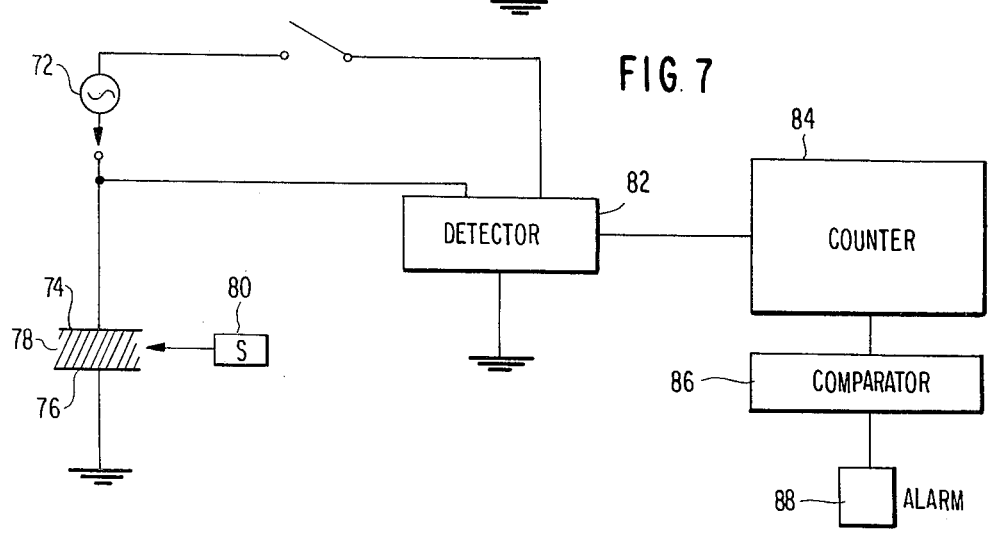
FIG. 7 illustrates another type of circuit that can determine change in conductance and which uses a detector and a counter circuit.

Another circuit arrangement is shown in FIG. 7 for detecting high dielectric bearing substances. The periodic frequency generating source 72 is connected across a capacitive element having spaced plates 74, 76 which have an air gap 78 between them. The sample 80 generally indicated at S is moved between the plates and the change in capacitance will be picked up in the detector 82. Ordinarily, the current is allowed to charge the capacitive plates 74, 76 until the voltage drop across them exceeds a preselected amount. At that time the detector cuts off the current such that the charge between the plates decays to a given level which then causes the detector to connect the current source back into the line to recharge the capacitor. With this arrangement the detector acts as a periodic voltage generator giving a signal the period of which is dependent upon the charging and discharging of the capacitive element. When the sample is inserted between the plates 74 and 76 the capacitance of the element is changed, and this in turn changes the output signal from the detector circuit 82 to the counter 84. The counter 84 supplies a signal to the comparator 86, and if this difference is sufficiently large the comparator will pass a signal to the alarm circuit 88 which will be activated.

The circuit is a fast acting circuit which is simple to construct. The drawback is that since the time constant of the capacitor is the product of both the resistance and capacitive elements, these component values cannot be readily determined.

Figure 8:
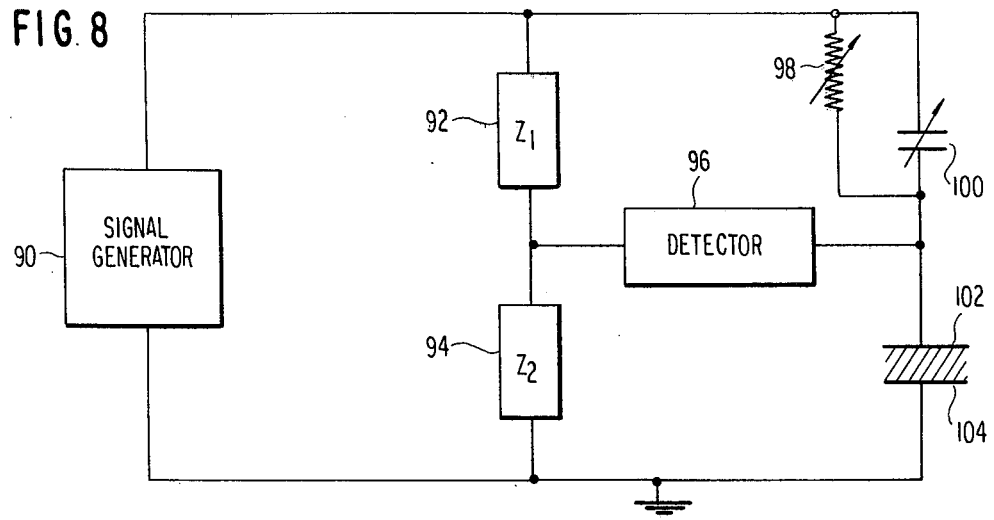
FIG. 8 is a block diagram of a bridge circuit which can be used to determine conductance change.

FIG. 8 shows the bridge circuit which is driven by a sine wave generator. Bridge elements 92 and 94 are balanced impedances which are connected by a detector 96. The detector will be nulled when the bridge is balanced. Variable resistance 98 and variable capacitor 100 match impedances Z1 shown as element 92. They also represent the equivalent circuit of the capacitive element in the remaining arm of the bridge formed by the parallel spaced plates 102 and 104.

The variable elements 98 and 100 effectively control the null position of the detector 96. A sample placed between the plates 102 and 104 can unbalance the bridge and rebalance is then obtained by adjusting elements 98 and 100. The adjustment gives the resistive and capacitive values introduced by the sample.

Again, it should be noted that some attention must be paid to the in-phase relationship of the applied periodic voltage. This circuit will be effective in obtaining signatures at various frequencies for the different types of explosive materials when identification is required. However, it should be noted that where frequencies are applied sequentially so as to obtain signature data, time must be allowed for manual or other manner of adjustment of the variable resistor and capacitor to rebalance the bridge.

The circuit of FIG. 8 can also be used as a calibrated bridge detector circuit. A known sample is placed between the plates 102 and 104 and will unbalance the bridge voltage. The quadrature components of the voltage unbalance are recorded and these are compared to known capacitive and resistance changes due to the sample. If these values do not agree with known values then the known values along with recorded values are used as a set of calibration numbers to correct further voltage readings to reflect true resistance and capacitive component data.

The data obtained on conductance for the various frequencies for a given sample will provide a conductance signature which can be stored and then subsequently compared with an unknown sample which is placed between the capacitor plates 102 and 104.

The detector circuit may include either a vector voltmeter, an AC voltmeter, a phase sensitive detector, or a digital computer.

With respect to identifying the type of dielectric material or the explosive, it should be noted that a number of frequencies must be applied to the bridge to obtain active data and this can be compared with the stored signatures for the various types of materials previously obtained.

A computer is used to perform this function, inasmuch as there is a requirement for storage of the sequentially obtained data numbers at each frequency and comparing them with the previously stored data. The technique can either use a comparative approach, or could very readily be adapted to a signal level or signal characteristic approach.

With respect to the system, it has also been found that data can be obtained which will give the location of an explosive in a package merely by observing and changing capacitance and conductance of the package as it passes between the plates. A reference point such as velocity of the envelope in its lateral passage or a time base can be used to sense the point at which the capacitive or conductance values change. With correlation of this data, the position of the explosive in the envelope or package can readily be determined.

As indicated above, the detector circuit may include a phase sensitive detector or a digital computer. It is possible to achieve the same results, however, with the use of Fourier transform techniques, for example by implementing digital Fourier transform systems such as a digital computer, or by using analog Fourier transform techniques, such as adaptive filters. The individual analog phase sensitive detectors for each frequency may be replaced by a broad band amplifier which, together with an accurate time base generator serving as a clock, make it possible to use the Fourier transform technique. The data may then be stuidied at fixed time intervals and analyzed by standard Fourier transform techniques in a computer, such as a mini computer. Advantageously, it is possible to employ, for this purpose, the same computer referred to above in connection with the identification of the type of dielectric material or explosive substance involved.

Figure 9:
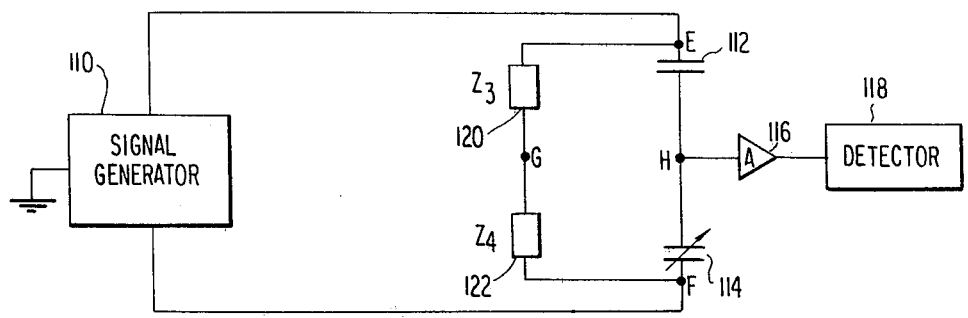
FIGS. 9 and 10 are block diagrams of bridge circuits of the invention.

FIG. 9 shows a bridge circuit in which signal generator 110 is a multi-frequency signal generator having a balanced output. The generator typically has a frequency range of about 100 hertz to 100 kilohertz. The signal generator is itself grounded and is connected across capacitive elements 112, 114. In the circuit illustrated in FIG. 9, each capacitive element 112, 114 consists of two parallel spaced plates. In practice, it is preferred to employ three parallel spaced plates, usually fabricated from the same material such as aluminum, or other suitable conductive material, with a guard ring circumferentially positioned on the midplate (see FIG. 10). This latter arrangement behaves as two capacitive elements arranged in series. Bridge elements 120, 122 are impedances which are connected in parallel to the capacitive elements 112, 114. The impedances 120, 122 may advantageously be precision metal film resistors and are matched as closely as possible to each other. The signal generator 110 is adjusted such that the potential value at points E and F sum to zero at all times. This results in the potential at point G being zero potential at all times. That is, if the potential at E is $V_e$ and the potential at F is $V_f$, then the desired condition is achieved when $V_e$ is equal to $-V_f$. Amplifier 116 is connected between the capacitive elements 112, 114 and is capable of converting current from the bridge circuit into a voltage output which can be detected by detector 118. This may involve a phase detector system or a Fourier transform system as discussed above. Although it may be possible to employ a resistor in place of amplifier 116 to convert the circuit current into a voltage output, the use of the amplifier is preferred as it is very sensitive to current and does not apply a load to the circuit. In addition, the amplifier 116 aids in maintaining a balanced potential at point H of the circuit. The capacitive elements 112, 114 are adjusted prior to placing any sample between the plates to give zero voltage output. This may be achieved by movement of one of the plates of the capacitive elements relative to a selected spacing of the plate or plates of the other capacitive element. The other capacitive element is then used as the detecting element. Thus, it is possible to balance the bridge circuit initially in a single operation, and no further balancing is required after each test sample has been placed in the detecting capacitive element. Occasionally, the test sample may generate a large response when placed in the capacitive element such that the voltage output of the amplifier 116 exceeds its dynamic range. When this occurs, it is possible to employ the other capacitive element to bring the voltage output down by nullifying at least a portion of the response so that the amplifier is again operating within its dynamic range. Preferably, this may be achieved by placing a substantially identical sample into the other capacitive element. Thus, for example, if one sample contains metal and the resulting voltage output exceeds the dynamic range of the amplifier, then insertion in the other capacitive element of a sample substantially identical to the first sample except for the metal will partially nullify the response output with respect to the common material and provide information in regard to the metal. This information can then be processed and compared with standard signatures using a computer as discussed above. The circuit illustrated in FIG. 9 thus has the advantages that first it is necessary to balance the system only once for each test run. Second, fast response time can be achieved due, in part, to the use of an amplifier which converts circuit current into an output voltage. Third, it is possible to employ greater plate spacing due to the complementary nature of the physical arrangement of the capacitive system together with the use of a guard ring. This allows for testing of samples of widely varying dimensions. When it is desired to test larger samples, it may be possible to arrange two or three sets of capacitive elements similar to the set 112, 114 in parallel with each other and to connect each set to its own amplifier and detector means. Alternatively, the amplifiers may be connected to a single detector. In this way, increased sensitivity can be achieved over a system which simply employs one set of plates of larger surface area.

Figure 10:
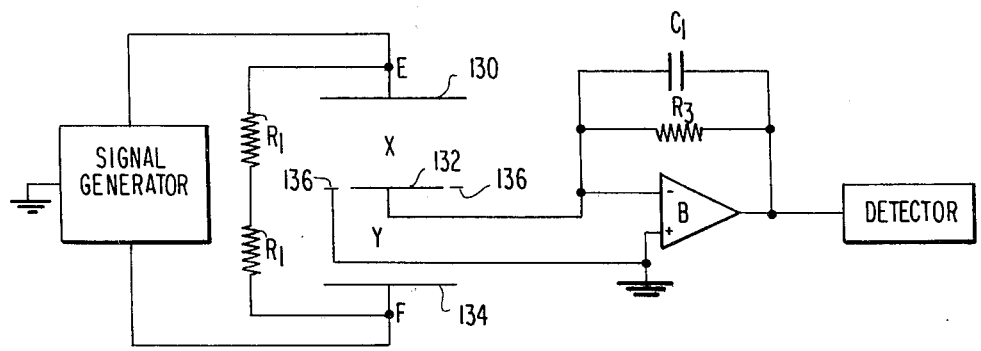

FIG. 10 shows a bridge circuit employing three space plates 130, 132, and 134, with a guard ring 136 circumferentially positioned on plate 132. As indicated earlier, this arrangement is the most preferred embodiment of this invention. Resistances $R_1$ and $R_2$ are equal in magnitude and are connected in parallel to the plates 130, 132 and 134. The guard ring 136 is grounded by the positive pole of a current to voltage amplifier B. A capacitor C1 and a resistor $R_3$ are connected in parallel with respect to each other and also with respect to the current voltage amplifier B. The capacitor C1 provides the gain and the resistor $R_3$ increases the stability of the system. The plates 130, 132 and 134 define a material sensing capacitive element X and a referencing capacitive element Y. In other respects, this bridge circuit is essentially the same as that shown in FIG. 9, and discussed in detail above.

A number of applications of this technique and circuitry include quality control in manufacturing processes, soil analysis for water concentration, analysis of tissue for fat concentration, and amount of contaminants in a fluid. In the latter instance there is a possibility of determining the amount of oil, sludge, or foreign materials in a water sample. It is also been found that the system and method of this invention, especially the embodiment shown in FIGS. 9 and 10, are particularly useful for monitoring and checking for the presence of explosives or drugs (such as heroine or cocaine) in packages, for example mail envelopes.

We claim:

1. Apparatus for identifying material having frequency responsive conductive and/or dielectric properties, comprising:

(a) capacitive means for producing an output signal and for producing a change in output signal when said material to be identified is brought within the influence of said capacitive means, said capacitive means including at least two capacitive elements, one of said capacitive elements being a material sensing capacitive element and another of said capacitive elements being a referencing capacitive element;

(b) frequency generating means for producing a balanced electrical output signal comprising plural preselected frequencies, said balanced output signal being applied across said capacitive means;

(c) capacitive response means connected to said capacitive means for evaluating the change in output signal from said capacitive means from an initial value determined in the absence of said material from the influence of said material sensing capacitive element to a different value obtained when said material is placed within the influence of said material sensing capacitive element;

(d) output signal component resolving means for resolving said change in output signal from said capacitive means into separate components which are a capacitive component and a conductive component, for each of said plural preselected frequencies, thereby to identify said material brought within the influence of said material sensing capacitive element.

2. Apparatus according to claim 1 wherein said material sensing capacitive element and said referencing capacitive element are defined by three spaced-apart capacitive plates, one of said capacitive plates being common to said material sensing capacitive element and said referencing capacitive element, said material sensing capacitive element and said referencing element having balanced capacitive and conductive values.

3. Apparatus according to claim 2 wherein said common capacitive plate is provided with a circumferential guard ring, said common capacitive plate being connected to a voltage means for converting current generated by said capacitive means into an output voltage.

4. Apparatus according to claim 1 wherein said plural preselected frequencies are applied simultaneously across said capacitive means.

5. Apparatus according to claim 1 wherein said plural preselected frequencies are applied sequentially across said capacitive means.

6. Apparatus according to claim 4 or claim 5 including a phase sensitive detector for evaluating said change in output signal from said capacitive means and resolving said change in output signal into said separate capacitive and conductive components, said apparatus further including computer means for identifying said material from said resolve separated capacitive and conductive components.

7. Apparatus according to claim 4, and further including a Fourier transform analyser for evaluating said change in output signal from said capacitive means and resolving said change in output signal into said separate capacitive and conductive components to identify said material.

8. Apparatus for identifying material having frequency responsive conductive and/or dielectric properties, comprising:

(a) capacitive means for producing an output signal and for producing a change in output signal when said material to be identified is brought within the influence of said capacitive means, said capacitive means including three spaced-apart capacitive plates defining two capacitive elements, one of said capacitive elements being a material sensing capacitive element and another of said capacitive elements being a referencing capacitive element, one of said capacitive plates being common to said material sensing capacitive element and said referencing capacitive element, said material sensing capacitive element and said referencing capacitive element having balanced capacitive and conductive values, said common capacitive plate being provided with a circumferential guard ring, said common capacitive plate being connected to a voltage means for converting current generated by said capacitive means into an output voltage;

(b) frequency generating means for producing a balanced electrical output signal comprising plural preselected frequencies, said balance output signal being applied across said capacitive means;

(c) capacitive response means connected to said capacitive means for evaluating the change in output signal from said capacitive means from an initial value determined in the absence of said material from the influence of said material sensing capacitive element to a different value obtained when said material is placed within the influence of said material sensing capacitive element;

(d) output signal component resolving means for resolving change in output signal from said capacitive means into separate components which are a capacitive component and a conductive component, for each of said plural preselected frequencies, thereby to identify said material brought within the influence of said material sensing capacitive element.

9. Method for identifying material having frequency responsive conductive and/or dielectric properties, said method comprising:

(a) providing a capacitive means for producing an output signal and for producing a change in output signal when a material to be identified is brought within the influence of said capacitive means, said capacitive means including at least two capacitive elements, one of said capacitive elements being a material sensing capacitive element and another of said capacitive elements being a referencing capacitive element;

(b) calibrating said capacitive means by balancing said material sensing capacitive element with said referencing capacitive element, and creating a known capacitance change in said sensing capacitive element to obtain a calibration output signal, said calibration output signal together with said known capacitance change being converted into calibration data;

(c) introducing said material to be identified into the influence of said material sensing capacitive element;

(d) measuring an output signal from said capacitive means caused by introducing said material to be identified into the influence of said material sensing capacitive element;

(e) resolving said output signal into separate components which are a capacitive component and a conductive component for each of said plural preselected frequencies; and (f) comparing said resolved capacitive and conductive components with said calibration data to identify the material brought within the influence of said material sensing capacitive element.

10. Method according to claim 9 wherein said known capacitance change is created by introducing a material of known capacitive effect into the influence of said material sensing capacitive element.

* * * * *